United States Patent [19]

Bunch

[11] 4,145,613
[45] Mar. 20, 1979

[54] MOTORIZED X-RAY TUBE ASSEMBLY
[75] Inventor: Laverne R. Bunch, Baltimore, Md.
[73] Assignee: CGR Medical Corporation, Baltimore, Md.
[21] Appl. No.: 845,132
[22] Filed: Oct. 25, 1977
[51] Int. Cl.$^2$ .................. G01N 21/34; G01N 23/04
[52] U.S. Cl. .............................. 250/445 T; 250/402; 250/491; 250/523
[58] Field of Search ............... 250/445 T, 445 R, 444, 250/446, 447, 448, 449, 450, 439 P, 522, 523, 524, 525, 490, 491, 402

[56] References Cited
U.S. PATENT DOCUMENTS

| 3,708,664 | 1/1973 | Bock et al. | 250/61.5 |
| 3,733,487 | 5/1973 | Louche et al. | 250/61.5 |

Primary Examiner—Craig E. Church
Assistant Examiner—Thomas P. O'Hare
Attorney, Agent, or Firm—Brady, O'Boyle & Gates

[57] ABSTRACT

A motorized device for rotating i.e. tilting the X-ray tube assembly in a linear and/or complex tomography radiographic system comprising the combination of a permanent magnet stepper motor coupled to a rotatable X-ray tube assembly through a helicon gear set and a spur gear set. The X-ray tube assembly incrementally rotates one angular step with each input drive pulse applied to the stepper motor from a pulse generator operated in accordance with a control input applied from an electronic control system in response to sensed positional change of the X-ray tube assembly. The stepper motor when unenergized is nevertheless adapted to provide a holding torque capability which eliminates the need for a separate brake assembly.

14 Claims, 6 Drawing Figures

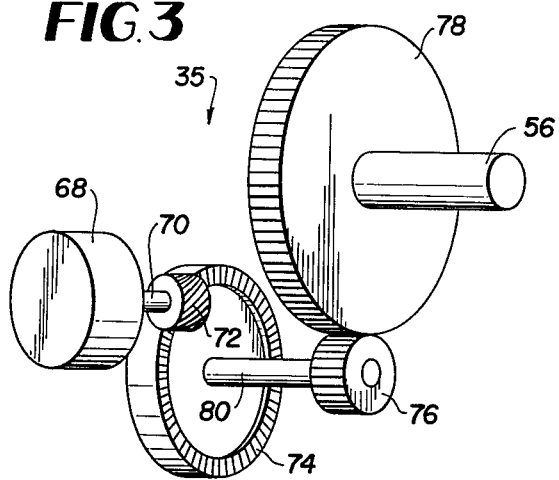
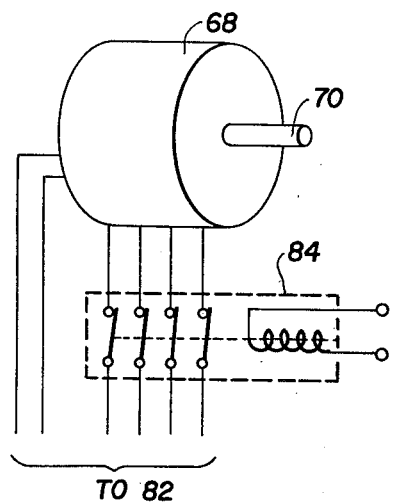
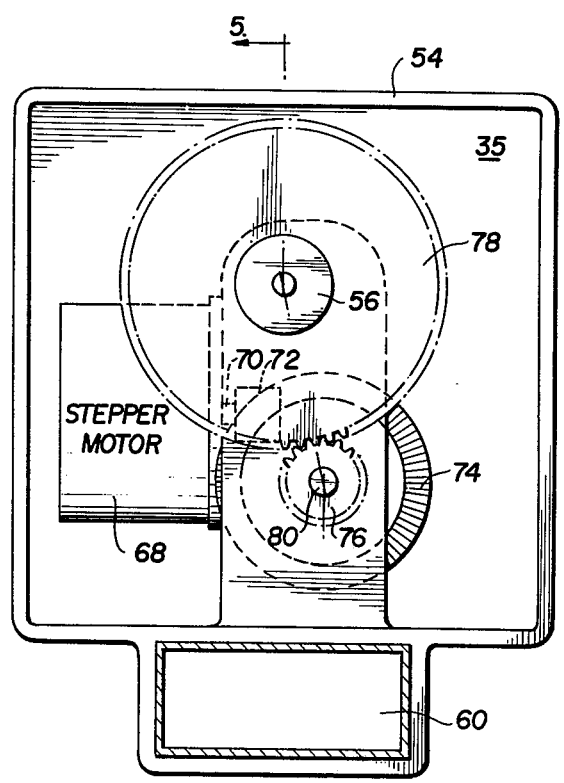
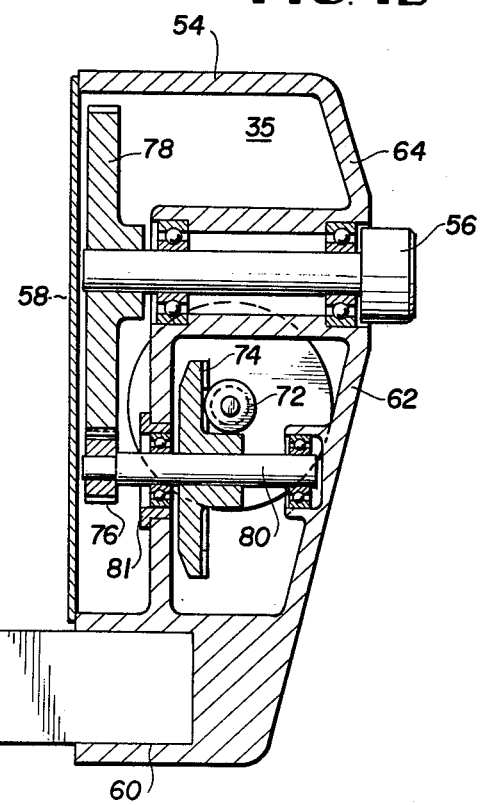

MOTORIZED X-RAY TUBE ASSEMBLY

CROSS REFERENCE TO RELATED APPLICATIONS

This invention is related to U.S. Ser. No 724,641, now U.S. Pat. No. 4,087,694 filed Sept. 20, 1976 entitled "Tomography System", M. J. Hellstrom, et al., to U.S. Ser. No. 739,017, now U.S. Pat. 4,095,110 filed Nov. 4, 1976, entitled, "Motorized Bucky", L. R. Bunch, and to U.S. Ser. No 835,738, filed Sept. 22, 1977, entitled, "A System for Circular and Complex Tomography", M. J. Hellstrom, which applications are all assigned to the present assignee.

BACKGROUND OF THE INVENTION

This invention relates generally to diagnostic X-ray apparatus and more particularly to a motor driven rotatable X-ray tube assembly which is adapted to be rotated or tilted with increased accuracy relative to a stationary or moving X-ray receptor while being capable of free wheeling for effortless manual positioning, yet preventing dangerous undesired motion if power is lost for any reason, thereby providing a fail-safe condition.

The electronic tomography system such as disclosed in the above referenced related applications, requires precise position and speed regulation of the X-ray tube assembly in relation to the X-ray receptor assembly which may be, for example, a bucky located under the X-ray examination table and which moves in synchronism therewith during a tomographic or other type of radiological procedure.

SUMMARY

It is the principal object of the present invention, therefore, to provide a new and improved means for progressively tilting an X-ray tube assembly located on a tube stand between predetermined angular excursions during a tomographic procedure, for example, which is not only simple in design, but eliminates the need for braking devices while providing the ability to be manually positioned while maintaining its orientation once positioned.

Briefly, the subject invention is directed to means for rotating an X-ray tube assembly about an axis parallel to an X-ray examination table in accordance with a control signal developed from the position of the X-ray tube assembly in relation to a predetermined reference, wherein the improvement comprises a housing having a rotational output shaft coupled to the X-ray tube assembly, which shaft is powered by spur gear assembly driven by means of a permanent magnet stepper motor through an intermediate helicon gear set assembly. The housing including these elements is attached to a mounting bar forming a part of a tube stand, which tube stand is adapted to be moved up and down, into and out of position relative to a patient, for example, on an X-ray examination table.

BRIEF DESCRIPTION OF THE DRAWINGS

FIG. 3 is a simplified perspective view of the spur gear and helicon gear assemblies utilized to rotate the X-ray tube assembly shown in FIG. 2;

FIG. 4A and 4B are front elevational and side elevational views partly in section of the housing incorporating the gear assemblies and stepper motor; and FIG. 5 is an electrical diagram illlustrative of the stepper motor configuration.

DESCRIPTION OF THE PREFERRED EMBODIMENT

Figure 1:
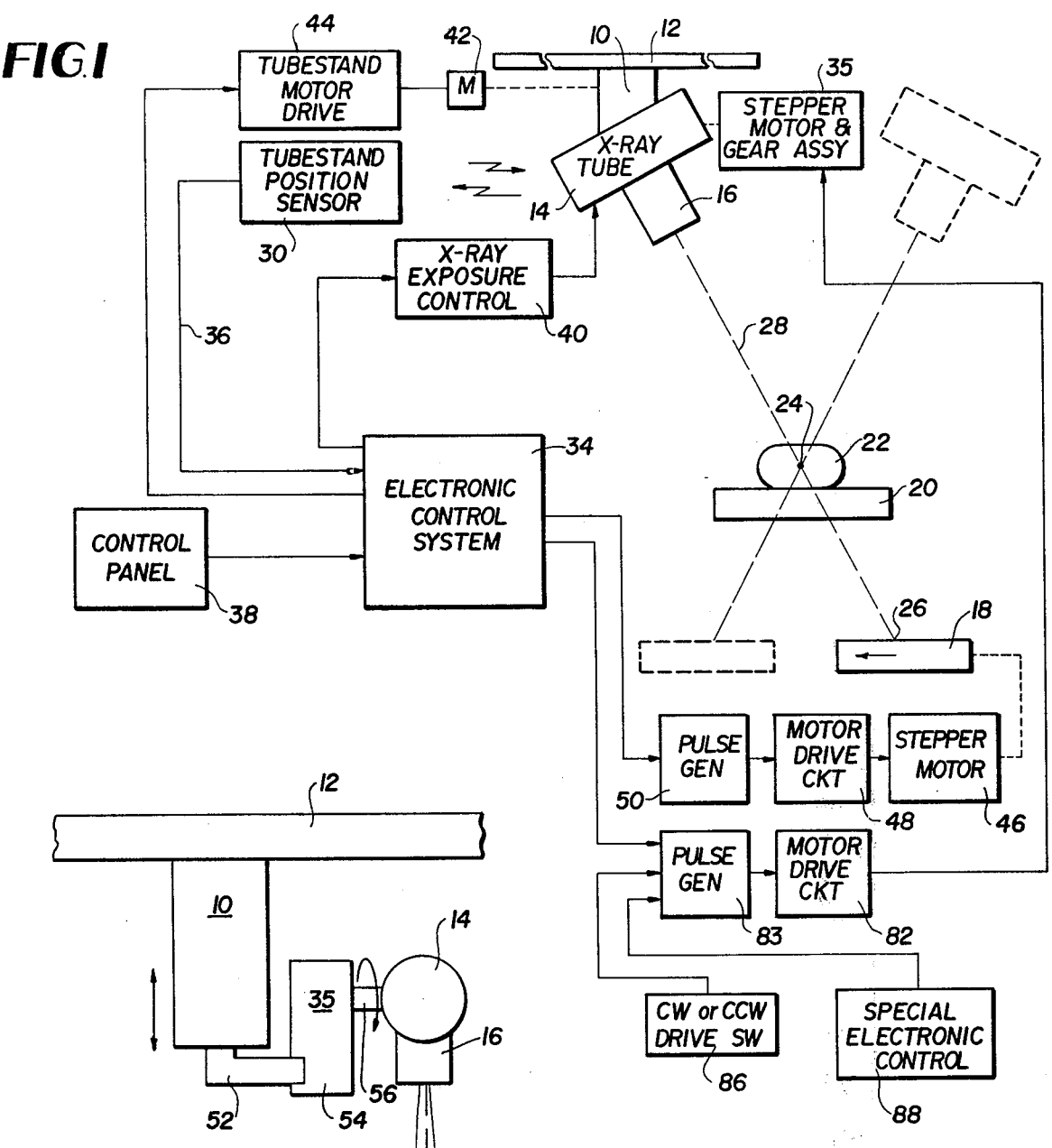
FIG. 1 is a block diagram illustrative of a tomographic system incorporating the subject invention.

Referring now to the drawings and more particularly to FIG. 1, reference numeral 10 denotes an X-ray tube suspension system commonly referred to as a tube-stand, which for purposes of illustration is mounted for translational movement on a ceiling structure 12. Mounted on the tube-stand 10 is an X-ray tube assembly 14 including an X-ray tube and collimator unit 16 attached thereto directed to a movable X-ray beam receptor 18 such as a film holder, commonly referred to as a bucky located beneath an X-ray examination table 20, upon which a patient 22 or other object under examination is located. In a linear tomographic procedure, for example, the tube-stand 10 including the X-ray tube assembly 14 and collimator 16 are moved or translated in one direction while the receptor 18 is synchronously moved in a mutually opposite direction. In order to maintain a constant point or fulcrum 24 within the patient 22 the X-ray tube 14 and collimator 16 must change its angular orientation as the tube-stand moves from side to side or orbits over the patient in order to accurately define an image point 26 on the receptor 18 in response to the X-ray beam 28 passing through the patient while blurring the surrounding image region.

As set forth in the above referenced related application U.S. Ser. No. 724,641, in order to provide a non-mechanical coupling between the X-ray tube 14 and the receptor 18 so that the central ray of the X-ray beam 28 always points to the same location, a tube-stand position sensor unit 30 is optically coupled to an optical reflector member 31 in the form of a corner tube prism which is located at a spot which is fixed relative to the focal spot of the X-ray tube 16.

The tube-stand position sensor 30 is shown in detail in the above reference related application and comprises a helium neon laser, not shown, which produces a monochromatic light beam which is directed to the reflector 31 through a beam expander and interferometer assembly. The tube-stand position and more particularly the linear translation of the tube-stand 10 results in an interferometer fringe pattern which is converted to an electrical pulse signal which in turn is coupled to an electronic control system 34 by means of electrical signal coupling means 36. The control system 34 operates in response to operator selected input parameters from a control panel 38 which parameters, for example, comprise fulcrum level, speed of sweep, and angle of sweep to first generate a control signal for operating an electrical drive motor 42 through a tube-stand motor drive unit 44 for linearly translating the tube-stand 10 to a START position and then in a predetermined sweep direction. An electronic control system 34 additionally responds to the pulse signals from the sensor unit 30 to control an electrical motor and gear drive assembly 35, the improvement comprising the subject invention and which is shown in detail in FIGS. 3, 4A and 4B for properly rotating i.e. tilting the X-ray tube 14 and its collimator 16 during a tomographic sweep. While a linear sweep is shown simply for purposes of illustration, the motor and gear drive assembly 34 is also adapted to rotate the X-ray tube and collimator properly for any type of movement, e.g. circular or complex motions of the X-ray source as disclosed in the related applicaton, Ser. No. 835,738. In a linear tomographic procedure, however, the tube-stand 10 and consequently the X-ray tube 14 moves in an opposite direction in relation to the receptor 18. The latter accordingly must follow the movement of the tube-stand with great precision. The movement of the receptor 18 is caused to be synchronized to the movement of the X-ray tube 14 by means of a permanent magnet stepper motor 46 coupled to a stepper motor drive circuit 48, which in turn receives a pulse train from a pulse generator 50 coupled to the electronic control system 34. This operation is disclosed in detail in the aforementioned related applications, U.S. Ser. Nos. 739,017 and 724,641.

Figure 2:
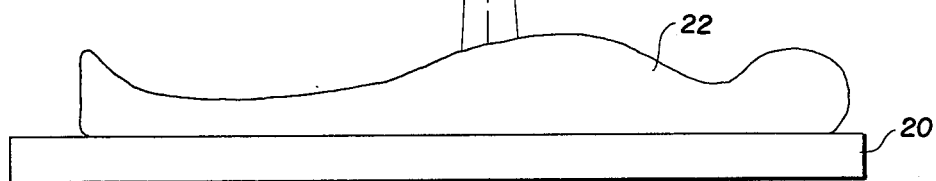
FIG. 2 is a simplified side elevation of an X-ray tube stand assembly with the subject invention located intermediate the tube stand assembly and the X-ray tube assembly.

Referring now more particularly to the subject invention, reference is now made to FIG. 2 where a simplified side elevational view of the X-ray tube 20 and patient 22 lying thereon is shown with the overhead tube-stand assembly 10 including a mounting bar 52 which is adapted to be moved to and from operational position as desired. On the mounting bar 52 is located the motor and gear drive assembly 35 located within a housing 54 having an output shaft 56 projecting therefrom upon which the X-ray tube 14 is mounted for rotation in a plane transverse to the longitudinal direction of the X-ray table 20.

Shown in FIGS. 3, 4A and 4B, the motor and gear drive assembly is comprised of a relatively flat rear wall portion 58 with a recess 60 at the lower portion thereof so as to be fitted on the mounting bar 52. Thus the entire assembly is adapted to be placed in relatively close relation to the tube-stand assembly 10. The output shaft 56 projects through the forward wall portion 62 having an upper and lower rearwardly sloping wall portion 64 and 66. The interior of the housing 54 is generally rectangular so as to accommodate a permanent magnet stepper motor 68, a typical example of which is a Model 091-FD90 manufactured by the Superior Electric Company. Such a motor exhibits a high torque to weight ratio, high speed, inherent damping for low noise, and relatively strong bearings. Moreover, such a motor exhibits the unusual characteristics of very low residual torque when the motor leads are unconnected i.e. open circuited and no voltage is applied but substantial residual torque necessary for "fail safe" operation when the motor leads are connected to form a closed circuit loop but no voltage is applied, and high holding torque when voltage is applied coupled with extremely high precision of rotation when operated with a suitable electronic drive circuit.

As shown in FIG. 4A, the shaft 70 of the stepper motor is connected to a helicon gear set consisting of a pinion gear 72 and a helicon gear 74. The gear ratio of the pinion and helicon gear set is in the range of from 10:1 to 20:1. The helicon gear 74 is coupled to the spur gear set consisting of a relatively small gear 76 and larger gear 78 through a coupling shaft 80 and backlash adjusting device 81. The two spur gears 76 and 78 preferably have a gear ratio of 5:1 with the larger gear 78 coupled to the output shaft 56. The combination of the helicon gear set and spur gear set provides a relatively compact front to back profile within the housing 54 making it particularly adapted to be positioned between the tube-stand 10 and the X-ray tube 14 as shown in FIG. 2.

The stepper motor 68 includes coil winding means, not shown, which is operated in accordance with signals applied thereto from a motor drive circuit 82 which has a pulse signal applied thereto, for example, from a pulse generator circuit 83 shown in FIG. 2, which in turn operates in accordance with an output from the electronic control system 34. A typical example of a stepper motor control circuit is shown in U.S. Pat. No. 4,035,708.

As shown in FIG. 5, while not necessary for proper operation but desirable, a normally closed electrical relay circuit 84 is coupled between the drive circuit 80 and the stepper motor 68. This relay circuit is also adapted to be located within the housing 54 and is operable to provide a small circulating current within the stepper motor when not receiving stepping pulses so as to cause the motor to provide a relatively high holding torque when the relay 84 is in its normally closed state; however, operation of the relay causes the relay contacts to open, which is adapted to provide an open circuit of the motor coil windings and accordingly will allow the output shaft 54 and the X-ray tube 14 connected thereto to back spin freely when desired. Additionally, when desirable, a manually operated clockwise or counter-clockwise selective switch circuit 86 is coupled to the pulse generator circuit 83 for causing the stepper motor 68 to operate independently of the control system 34 to effect a desired rotation of the X-ray tube assembly 14 in one direction or the other when one or more switches are depressed but becoming inoperative to stop rotation when released. Also a special procedure control system 88 similar to the control system 34 but programmed to perform a rotational drive of the X-ray tube assembly to any desired angle during special X-ray procedures can, when desirable, be coupled to the pulse generator circuit 83.

Thus what has been shown and described is a stepper motor and rotational gear drive assembly which provides relatively high output torque when used as a motorized drive for rotating an X-ray tube while providing high holding torque when used as a brake. The combination of the helicon gear set and spur gear set coupled to the stepper motor provides a very compact drive and brake with extremely high efficiency and being particularly adapted to meet the positional requirements of a highly complex radiological diagnostic system. The gear set combination permits backlash to be substantially eliminated while providing a positional accuracy of the output shaft in the order of 2 arc minutes. Moreover, such a configuration as disclosed provides a mechanism whose weight, volume and cost is less than for a conventional electromechanical brake assembly utilized in connection with this type of radiological apparatus.

While there has been shown and described what is at present considered to be the preferred embodiment of the subject invention, modifications will readily occur to those skilled in the art. It is not desired, therefore, that invention be limited to the specific arrangement shown and described, but it is to be understood that all equivalents, alterations and modifications coming within the spirit and scope of the present invention are herein meant to be included.

Accordingly, I claim:

1. Apparatus including an X-ray source, an X-ray detector and means for rotating the X-ray source on a mounting structure relative to the X-ray receptor, comprising the improvement of:
- a housing attached to said mounting structure and having a rotatable output shaft coupled to said X-ray source;
- a spur gear set consisting of a plurality of intermeshed spur gears located within said housing and coupled to said output shaft;
- a helicon gear set consisting of a pinion gear and a helicon gear located within said housing and including means for coupling said helicon gear to said spur gear set;
- electrical stepper motor means having a rotary output shaft coupled to said pinion gear and being responsive to drive pulses applied thereto to incrementally rotate said output shaft in a predetermined direction for each drive pulse applied; and
- drive pulse circuit means coupled to said stepper motor and being operable to generate said drive pulses in response to a command signal applied thereto, said drive pulse circuit being operable to generate said drive pulses in response to positional change of said X-ray source and wherein said X-ray receptor is moved in an opposite direction with respect to the direction of the positional change of said X-ray source.

2. The apparatus as defined by claim 1 wherein said stepper motor means is located within said housing.

3. The apparatus as defined by claim 1 wherein said spur gear set is comprised of a first and second spur gear wherein said first spur gear has a relatively smaller number of teeth than said second spur gear, and wherein said second spur gear is coupled to said output shaft.

4. The apparatus as defined by claim 3 wherein the gear ratio of said first and second spur gears is 5:1.

5. The apparatus as defined by claim 1 wherein the gear ratio of said helicon gear to said pinion gear of said helicon gear set is in the range of from 10:1 to 20:1.

6. The apparatus as defined by claim 1 wherein said electrical stepper motor includes motor coil winding means coupled to said drive circuit means; and
additionally including normally closed switch means connected between said motor coil winding means and said drive pulse circuit means for maintaining a closed loop therebetween, thereby providing a residual torque on said output shaft in absence of drive pulses being applied thereto.

7. The apparatus as defined by claim 6 wherein said normally closed switch means comprises a normally closed relay circuit which is adapted to be selectively operated and provide an open circuit between said motor coil winding means and said pulse circuit means to permit the X-ray tube source to rotate freely when desired.

8. The apparatus as defined by claim 1 wherein said drive pulse circuit includes electrical pulse generator means providing electrical drive pulses of predetermined polarity for operating said stepper motor to rotate said X-ray tube in a predetermined direction with respect to the direction of the positional change of said X-ray source tube to direct an X-ray beam to an X-ray receptor moving in an opposite direction with respect to the direction of the positional change of said X-ray source.

9. The apparatus as defined by claim 8 and additionally including stepper motor drive means coupled between said pulse generator and said stepper motor.

10. The apparatus as defined by claim 9 whereby said stepper motor comprises a permanent magnet stepper motor.

11. The apparatus as defined by claim 9 and additionally including control circuit means operative to provide an electrical control signal coupled to said pulse generator means for performing a predetermined X-ray procedure.

12. The apparatus as defined by claim 11 wherein said control circuit means operates in response to a sensed positional change of said X-ray source.

13. The apparatus as defined by claim 11 wherein said control circuit means operates to effect a rotational drive of said X-ray source to any desired angle during said predetermined X-ray procedure.

14. The apparatus as defined by claim 9 and additionally including manually operable circuit means coupled to said control circuit means for providing a rotational drive of said X-ray in a predetermined direction while said circuit means is maintained manually operable.

* * * * *